United States Patent
Senthilkumar et al.

(10) Patent No.: US 7,345,169 B2
(45) Date of Patent: *Mar. 18, 2008

(54) PROCESS FOR THE PREPARATION OF CEPHALOSPORIN ANTIBIOTIC

(75) Inventors: Udayampalayam P. Senthilkumar, Chennai (IN); Kanagaraj Sureshkumar, Chennai (IN); Singaravel Mohan, Chennai (IN); Lakshminarayanan Arunkumar, Chennai (IN)

(73) Assignee: Orchid Chemicals & Pharmaceuticals Ltd., Chennai (IN)

( * ) Notice: Subject to any disclaimer, the term of this patent is extended or adjusted under 35 U.S.C. 154(b) by 0 days.

This patent is subject to a terminal disclaimer.

(21) Appl. No.: 11/240,382

(22) Filed: Oct. 3, 2005

(65) Prior Publication Data

US 2006/0058281 A1 Mar. 16, 2006

Related U.S. Application Data

(63) Continuation-in-part of application No. 10/922,991, filed on Aug. 23, 2004.

(30) Foreign Application Priority Data

Aug. 22, 2003 (IN) .......................... 673/CHE/2003

(51) Int. Cl.
*C07D 501/36* (2006.01)
(52) U.S. Cl. ....................................... 544/227; 544/226
(58) Field of Classification Search ...................... None
See application file for complete search history.

(56) References Cited

U.S. PATENT DOCUMENTS

| | | | | |
|---|---|---|---|---|
| 4,153,631 | A * | 5/1979 | Bader et al. ................. | 568/315 |
| 4,298,529 | A | 11/1981 | Ueda et al. | |
| 4,464,367 | A | 8/1984 | Labeeuw et al. | |
| 4,937,330 | A | 6/1990 | Sacks et al. | |
| 5,109,131 | A | 4/1992 | Naito et al. | |
| 6,218,380 | B1 * | 4/2001 | Cole et al. ............. | 514/210.06 |
| 6,458,949 | B1 * | 10/2002 | Handa et al. ................ | 540/226 |
| 6,552,186 | B2 | 4/2003 | Gerlach et al. | |
| 6,777,549 | B2 | 8/2004 | Gerlach et al. | |
| 6,800,756 | B2 * | 10/2004 | Deshpande et al. ......... | 540/226 |
| 6,919,449 | B2 * | 7/2005 | Deshpande et al. ......... | 540/222 |
| 7,071,329 | B2 * | 7/2006 | Monguzzi et al. .......... | 540/226 |
| 2003/0087318 | A1 * | 5/2003 | Lallone ...................... | 435/7.23 |
| 2005/0020561 | A1 | 1/2005 | Kumar et al. | |
| 2005/0059820 | A1 | 3/2005 | Datta et al. | |
| 2005/0080070 | A1 * | 4/2005 | Deshpande et al. ......... | 514/202 |
| 2005/0119244 | A1 * | 6/2005 | Monguzzi et al. .......... | 514/202 |
| 2005/0119478 | A1 * | 6/2005 | Monguzzi et al. .......... | 540/227 |
| 2005/0143392 | A1 * | 6/2005 | Naik et al. ............. | 514/254.09 |
| 2006/0094872 | A1 * | 5/2006 | Senthilkumar et al. ..... | 540/217 |
| 2006/0199836 | A1 * | 9/2006 | Turtle et al. ................. | 514/301 |
| 2006/0264417 | A1 * | 11/2006 | Olson et al. ........... | 514/212.03 |
| 2006/0264507 | A1 * | 11/2006 | Tanoury et al. ............. | 514/554 |
| 2007/0100143 | A1 * | 5/2007 | Parthasaradhi Reddy et al. .......................... | 544/284 |

FOREIGN PATENT DOCUMENTS

| | | |
|---|---|---|
| CA | 1146165 | 5/1983 |
| EP | 0 030294 A2 | 6/1981 |
| EP | 0 842 937 A2 | 5/1998 |
| GB | 2 012 276 A1 | 7/1979 |
| WO | WO 00/63214 | 10/2000 |
| WO | WO 02/083634 A2 | 10/2002 |
| WO | WO 2004/058695 A1 | 7/2004 |
| WO | WO 2004/092183 A2 | 10/2004 |

OTHER PUBLICATIONS

Turner, "The Design of Organic Synthesis" (Elsevier, 1976), pp. 10 and 149.*
Mayer et al., Chem Soc. Rev., 30, 332 (2001).*
Chen et al., Angewandte Chemie Int. Ed. vol. 37, Issue 1/2, pp. 91-93 (1998).*
Science 310, p. 409 (Oct. 21, 2005).*
"Distillation" (Wikipedia)<http://en.wikipedia.org/wiki/Distillation> (retrieved from the internet Apr. 18, 2007).*

* cited by examiner

*Primary Examiner*—Mark L Berch
(74) *Attorney, Agent, or Firm*—Oliff & Berridge, PLC

(57) ABSTRACT

An improved one-pot process for the preparation of Ceftiofur of the formula (I) or its salt, without isolating intermediate compound (I)

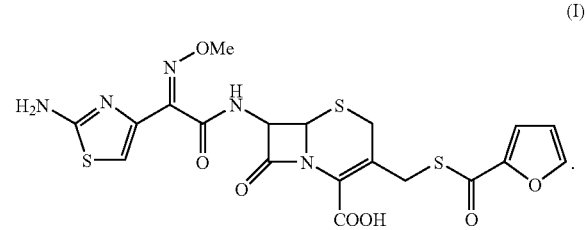

7 Claims, No Drawings

US 7,345,169 B2

PROCESS FOR THE PREPARATION OF CEPHALOSPORIN ANTIBIOTIC

FIELD OF THE INVENTION

This application is continuation in part application of our co-pending application Ser. No. 10/922,991, which claims priority from 673/CHE/2003 filed on Aug. 22, 2003. The present invention relates to a process for the preparation of cephalosporin antibiotic of the formula (I), more particularly relates to preparation of Ceftiofur of formula (I).

(I)

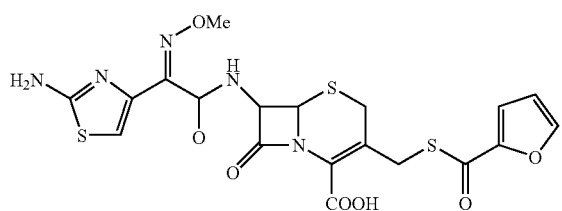

BACKGROUND OF THE INVENTION

Ceftiofur, a semisynthetic cephalosporin, is a broad-spectrum antibiotic against both Gram-positive and Gram-negative bacteria including beta-lactamase-producing bacterial strains and anaerobes. Its antibacterial activity results from the inhibition of mucopeptide synthesis in the cell wall in a similar fashion to other cephalosporins. Ceftiofur is used in the treatment of respiratory infections in cattle and pigs. The chemical designation is [6R-[6a,7b(z)]]-7-[[(2-amino-4-thiazolyl) (methoxyimino)acetyl]amino]-3-[[2-furanylcarbonyl)thio]methyl]-8-oxo-5-thia-1-azabicyclo[4.2.0]oct-2-ene-2-carboxylic acid. The sodium and hydrochloride salts are administered intramuscularly and intravenously.

Ceftiofur is first disclosed in U.S. Pat. No. 4,464,367, which also discloses a process for preparing Ceftiofur and its sodium salt.

There are various literature methods reported for the preparation of cephalosporin compounds like Ceftiofur which are summarized below:

U.S. Pat. No. 5,109,131 describes a process in which 4-halo-2-methoxyimino-3-oxobutyric acid, is reacted with cephem moiety as per the scheme depicted below:

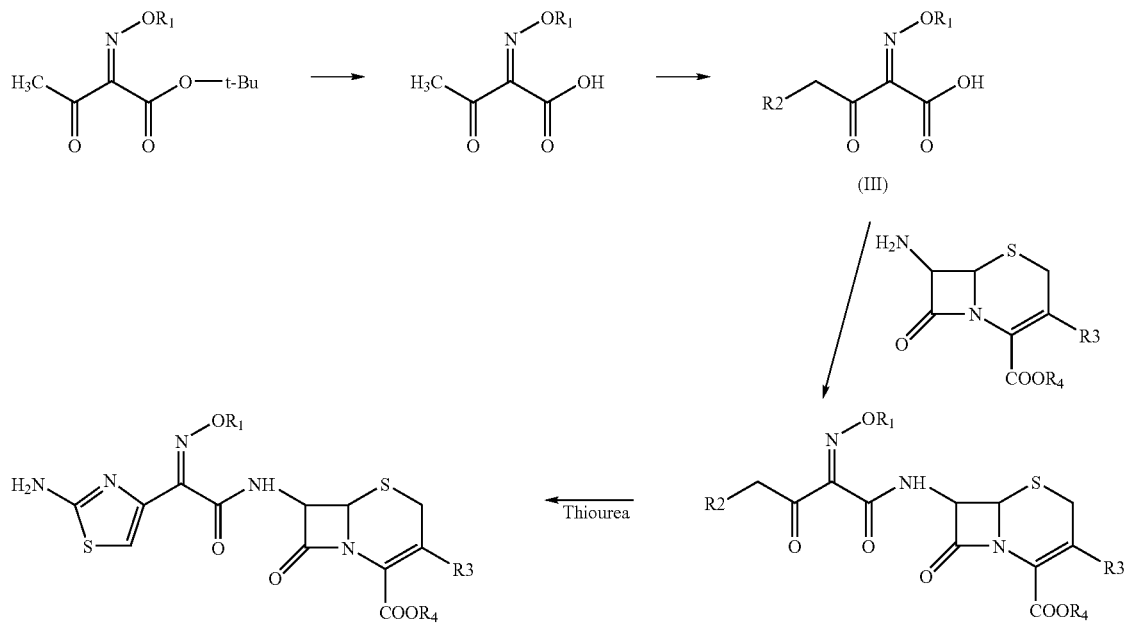

wherein $R_1$ stands for a $C_{1-4}$ alkyl group optionally substituted with carboxyl or a $C_{1-4}$ alkoxy-carbonyl group, $R_2$ stands for a halogen atom, $R_3$ stands for hydrogen atom or a standard cephalosporin substituent which includes Ceftiofur also, and $R_4$ stands for hydrogen atom or a group which can be converted to hydrogen U.S. Pat. No. 4,298,529 describes a similar process as depicted in U.S. Pat. No. 5,109,131, according to this patent the cephem compound of formula may be used as such or as a silyl derivative (column 12, lines 20-23 of U.S. Pat. No. 4,298,529).

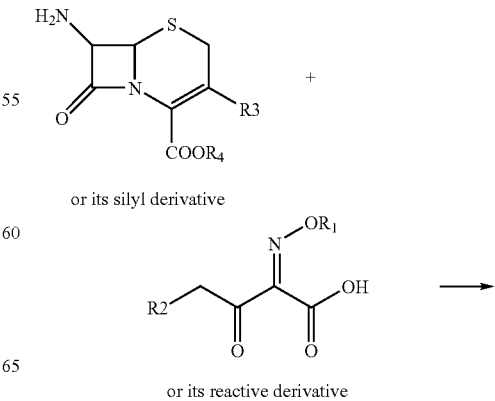

or its silyl derivative or its reactive derivative

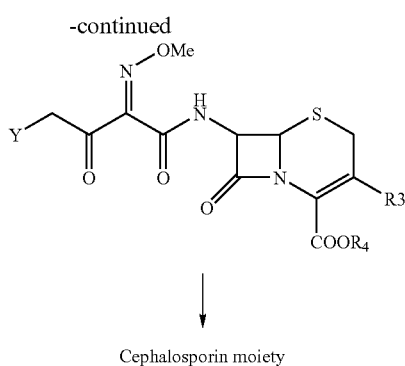

Cephalosporin moiety

CA 1,146,165, also discloses a similar approach for the preparation of cephalosporin compounds.

EP 0030294 discloses a process for the preparation of compound of cephalosporin antibiotic as given in scheme 1:

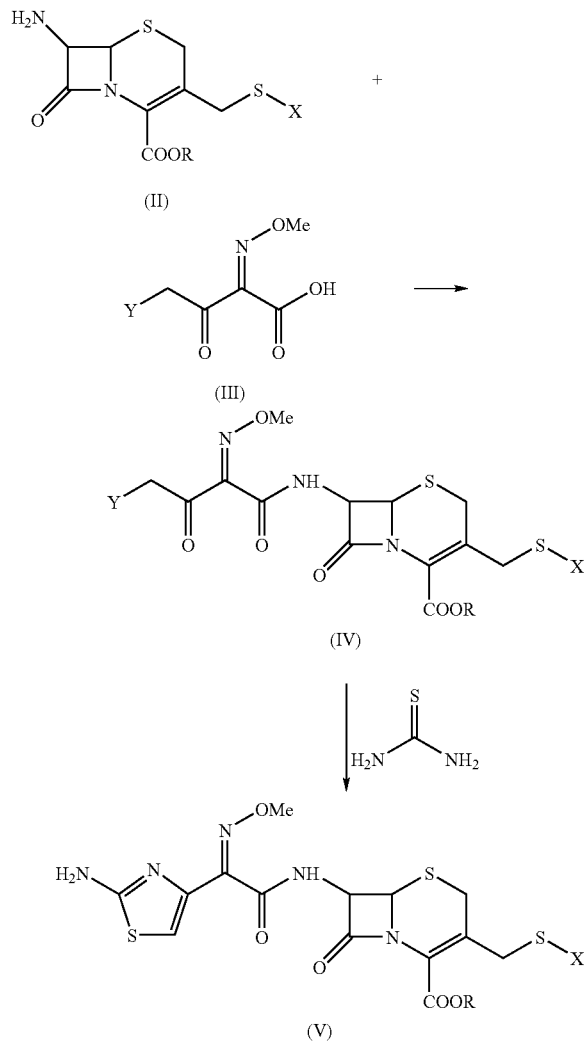

wherein R represents hydrogen atom or a readily hydrolysable ester group and X represents one of the groups GB 2012276 describes 7-(4-halogeno-3-oxo-2-alkoxy-iminobutyrylamino) cephalosporin derivative of the formula (XIII)

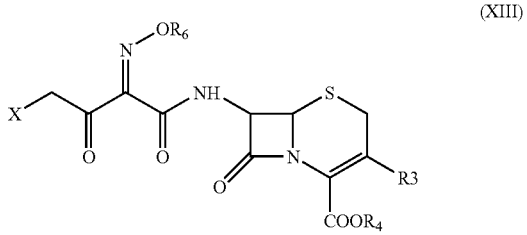

wherein X represents a halogen atom, $R^3$ represents —$CH_2R^5$ ($R^5$ is hydrogen atom or the residue of a nucleophilic compound), a halogen atom, an alkoxyl group, thiol group, amino group etc., —$COOR^4$ represents a carboxylic group which may be esterified, and $R^6$ represents an alkyl group and also a process for preparing a 7-[2-(2-aminothiazol-4-yl)-2-(syn)-alkoxyiminoacetamido] cephalosporin derivatives of the formula (XIV)

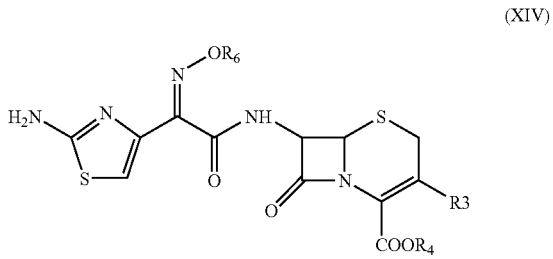

U.S. Pat. No. 6,552,186 relates to the preparation of ceftriaxone and cefotaxime also claims a process for the preparation of number of cephalosporin antibiotic including Ceftiofur using similar approach disclosed in prior art. As cited by US publication No. 2005/0059820, this patent itself obvious and anticipated over prior art. Moreover this patent utilizes two phase solvent system, the one of the disadvantages with the two phase solvent system in cyclization with thiourea stage is that the reaction takes more times to completion or many times reaction will not complete and leaves 7 to 15% starting material; also yield less pure API.

Thus the above literature reports like CA 1,146,165, U.S. Pat. No. 4,298,529 and U.S. Pat. No. 5,109,131 (which are published after the grant of U.S. Pat. No. 4,464,367, where Ceftiofur is first disclosed) and U.S. Pat. No. 6,552,186 pertaining towards the preparation of Cephalosporin antibiotics suggests and teaches the following general scheme for the preparation of Ceftiofur of formula (I):

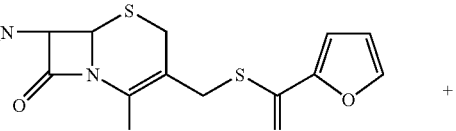

or its reactive derivative
(A)

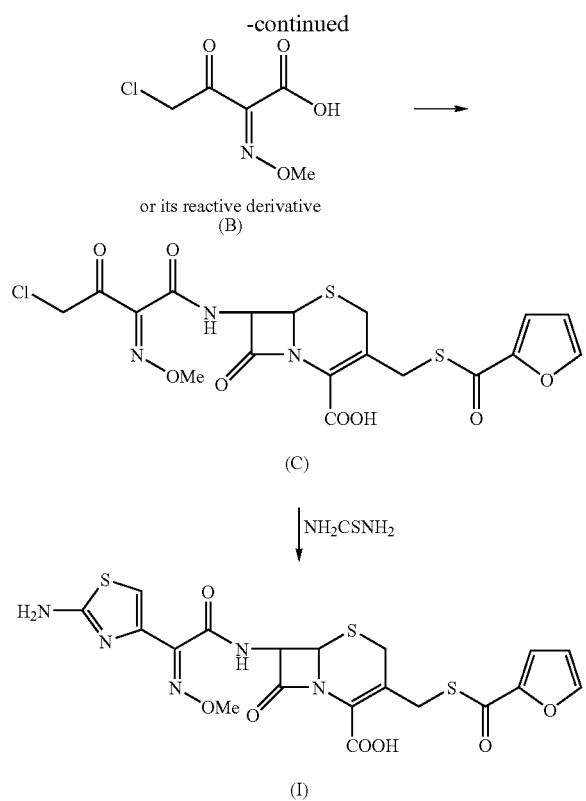

Though the literature pertains to cephalosporin chemistry, which suggests or motivates the above general process, U.S. Pat. No. 6,458,949 claims a similar process for preparing Ceftiofur. According to this patent the purity of final Ceftiofur depends on the isolation of compound of formula (C). This patent also acknowledges that cyclization of compound of formula (C) in-situ with thiourea in the presence base yield impure Ceftiofur and further purifications are difficult, time consuming and do not result in a product of good quality. Also this patent claims the compound of formula (C) though it is obvious over cephalosporin chemistry.

In our continued research we have identified a process for the preparation of Ceftiofur, in which even though the compound of formula (C) is not isolated, yield Ceftiofur in highly pure form, whereby avoiding the time consuming filtration step and makes overall process commercially viable and economical. None of the prior art suggest or event motivates the present invention.

OBJECTIVES OF THE INVENTION

The primary objective of the invention is to provide an improved process for the preparation of cephalosporin antibiotic of the formula (I), without isolating the compound of formula (IV).

Another objective of the present invention is to provide an improved process for the preparation of Ceftiofur of the formula (I) in high purity and yield.

One more objective of the present invention provides Ceftiofur TFA salt.

SUMMARY OF THE INVENTION

Accordingly, the present invention provides an improved process for the preparation of Ceftiofur of the formula (I)

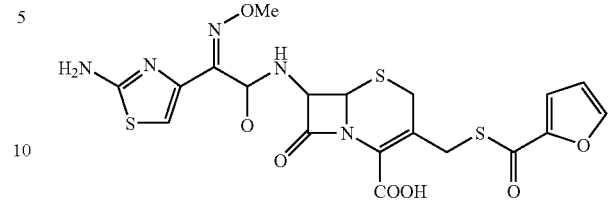

which comprises:
(i) activating the compound of formula (III) as acid chloride of formula (IIIa) in an organic solvent

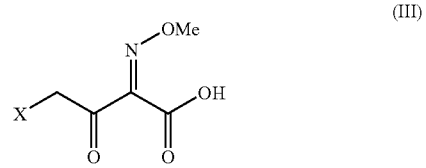

where X represents halogen atom such as chlorine or bromine, using a halogenating agent,
(ii) treating the reaction mass obtained from step (i) with water at a temperature in the range of −40° C. to 10° C.,
(iii) separating the organic layer containing the activated derivative of formula (IIIa) and condensing the activated derivative of the formula (IIIa)

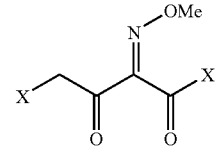

where X represents halogen atom such as chlorine or bromine, with 7-amino cephalosporin derivative of the formula (II) or its reactive derivative

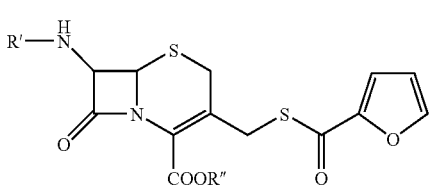

wherein R' represents hydrogen, or silyl and R" represents hydrogen or silyl in the presence of a solvent and in the presence or absence of base at a temperature in the range of −50° C. to 10° C. to produce a compound of formula (IV)

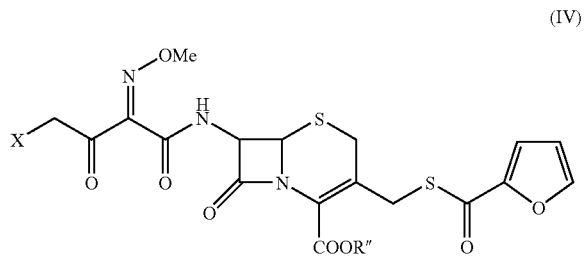

where all symbols are as defined above, and iv) optionally removing the solvent of step (iii) reaction mass and cyclizing the compound of formula (IV) with thiourea, water, in the presence or absence of 'water miscible solvent' and base at a temperature in the range of −50 to 30° C. to produce compound of formula (I) or its salt, wherein the improvement consists of producing the compound of formula (I), without isolating compound of formula (IV) and also characterized by one or more of the following improvements:
a) removing the solvent in step (iii),
b) conducting the reaction of step (iv) in homogeneous solvent system.

DETAILED DESCRIPTION OF THE INVENTION

In an embodiment of the present invention the halogenating agent for activating the acid of formula (III) is selected from $PCl_5$, $PCl_3$, $POCl_3$, $SOCl_2$ and the like, and the organic solvent employed in step (i) is selected from dichloromethane, ethyl acetate, THF, DMF and the like or any inert solvent can be employed.

In another embodiment of the present invention the treatment of step (i) reaction mass with water at low temperatures removes the impurities formed. Because of this treatment, Ceftiofur was obtained in pure form even without isolating the compound of formula (IV). This constitute one of the advantage of the present invention.

In still another embodiment of the present invention, the condensation of compound of formula (II) with (III) is performed in the presence of a solvent selected from dichloromethane, ethyl acetate, methanol, ethanol, isopropanol, isobutyl alcohol, n-propanol, n-butanol, tert-butanol, tetrahydrofuran, aromatic hydrocarbons, acetone, ethyl methyl ketone, diethyl ketone, pentan-3-one, cyclohexanone, methyl isobutyl ketone, dioxane, acetonitrile, DMAc, N,N-dimethylformamide, dialkylethers, ethylene glycol, ethylene glycol monomethyl ether, diglyme, monoglyme, diethylene glycol, triethylene glycol, polyethylene glycol, water and the like or mixtures thereof.

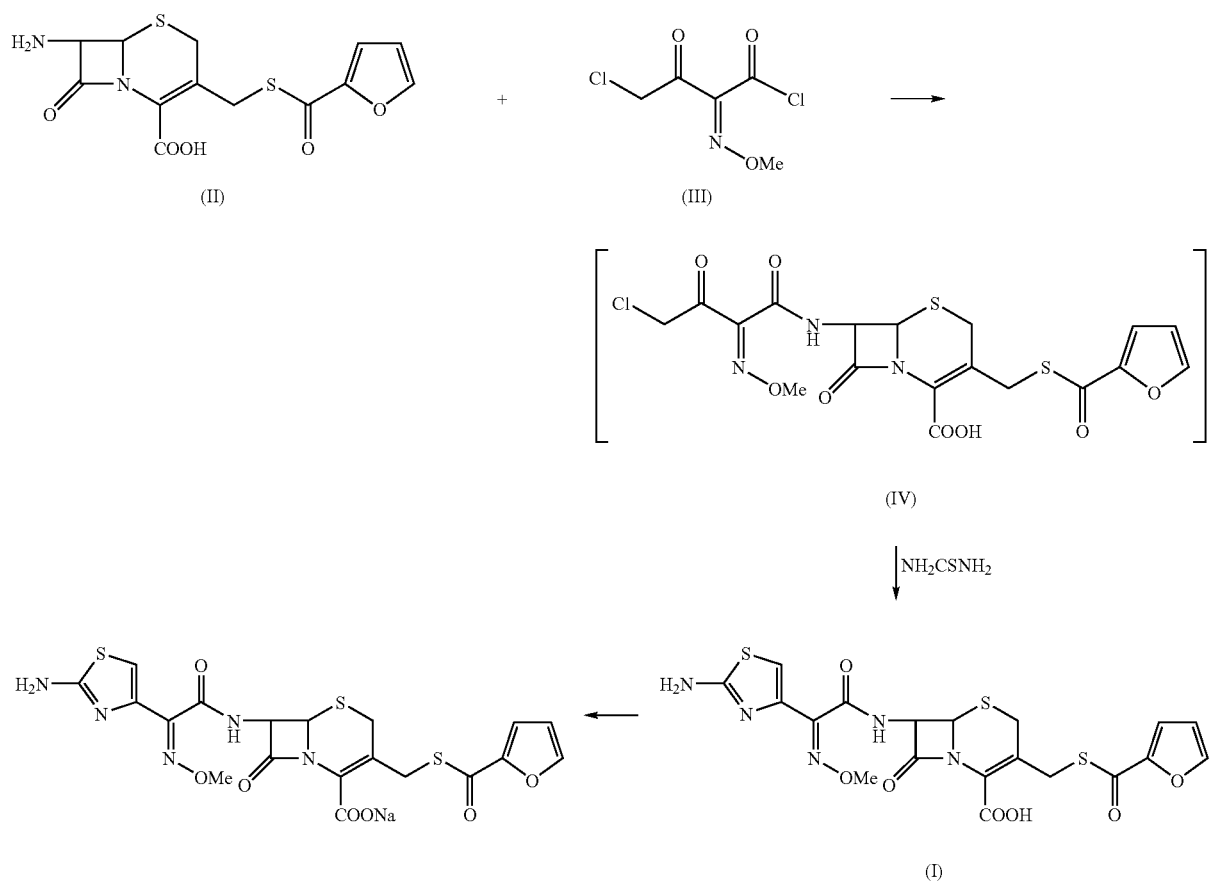

In yet another embodiment of the present invention, the base used for maintaining the pH is selected from ammonia, sodium carbonate, sodium bicarbonate, ammonium carbonate, potassium carbonate, sodium hydroxide, potassium hydroxide, trimethyl amine and the like. The presence of base facilitates the condensation, when the compound of formula (II) is employed in free form.

In yet another embodiment of the present invention, the compound of formula (IV) is prepared by condensing the reactive derivative of compound of formula (II), wherein the reactive derivate is silylated form of formula (II), with (III). Silylated form of formula (II) is prepared by treating the compound of formula (II) with silylating agents like hexamethyldisilazane (HMDS), trimethylsilyl chloride (TMCS), bistrimethylsilyl urea (BSU), N,O-Bistrimethylsilyl acetamide (BSA) and the like in the presence or absence of catalyst like N-methyl morpholine, acetamide and imidazole. The solvent used for silylation and subsequent condensation is selected from dichloromethane, N,N-dimethylformamide, N,N-dimethylacetamide, acetonitrile, toluene and the like or mixtures thereof more particularly dichloromethane.

In another embodiment of the present invention the solvent employed for silylation and subsequent condensation can be removed by distillation so as to conduct the cyclization in homogeneous solvent system. Conventional method involves quenching of this reaction mass to methanol or water. However, it has been observed the impurity formation in conventional method is high when compared to distillation, which is an advantage of the present invention. It has been also observed that the conventional two-phase solvent system takes more time for cyclization, and produces less pure Ceftiofur.

In still another embodiment of the present invention the present invention was performed without isolating the compound of formula (IV), also the reaction was performed in one pot, which is also one of the advantages of the present invention.

In yet another embodiment of the present invention the cyclization of compound of (IV) is carried out using water miscible solvent selected from tetrahydrofuran, acetone, ethyl methyl ketone, methyl isobutyl ketone, methyl isopropyl ketone, cyclohexanone, diethyl ketone, pentan-3-one, cyclohexanone, acetonitrile, N,N-dimethylformamide, N,N-dimethylacetamide, dioxane, ($C_1$-$C_5$) alcohol, ethylene glycol, diglyme, monoglyme, ethylene glycol monomethyl ether, diethylene glycol, triethylene glycol, polyethylene glycol and the like or mixtures there of; and base employed is selected from sodium acetate, sodium carbonate, sodium bicarbonate, potassium acetate, ammonium acetate, ammonium carbonate, barium carbonate, calcium carbonate, potassium carbonate, barium carbonate, lithium carbonate, potassium bicarbonate, sodium methoxide, triethyl amine, isopropyl amine, sodium ethoxide and the like.

It is one of the advantage of the present invention, salt of Ceftiofur like pure Ceftiofur sodium, Ceftiofur TFA, Ceftiofur HCl, Ceftiofur sulphate can be prepared directly from the reaction solution itself, thereby avoiding the conventional process, which involve converting Ceftiofur in free form to Ceftiofur sodium. In another embodiment of the present invention the high pure Ceftiofur of formula (I) obtained by converting Ceftiofur sodium into Ceftiofur TFA or sulphate salt, which in turn converted to Ceftiofur sodium. Accordingly, the present invention provides novel Ceftiofur TFA salt and Ceftiofur sulphate salt.

In one more embodiment of the present invention, the invention can be extended to the preparation of other cephalosporin antibiotics as described in our co-pending application Ser. No. 10/922,991, accordingly this invention provides a process for the preparation of cephalosporin antibiotic of the formula (I)

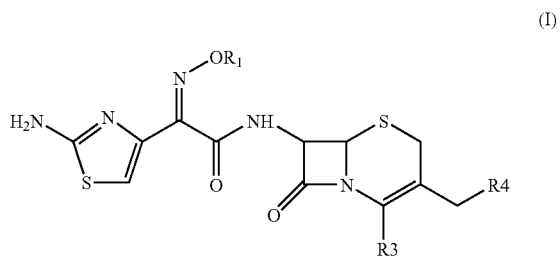

wherein $R_1$ represents hydrogen, trityl, $CH_3$, $CR_aR_bCOOR_c$ where $R_a$ and $R_b$ independently represent hydrogen or methyl and $R_c$ represents hydrogen or ($C_1$-$C_6$) alkyl; $R_3$ is carboxylate ion or $COOR_d$, where $R_d$ represents hydrogen, ester or a counter ion which forms a salt; $R_4$ represents H, $OCH_3$, $OCOCH_3$, =$CH_2$, $OCONH_2$,

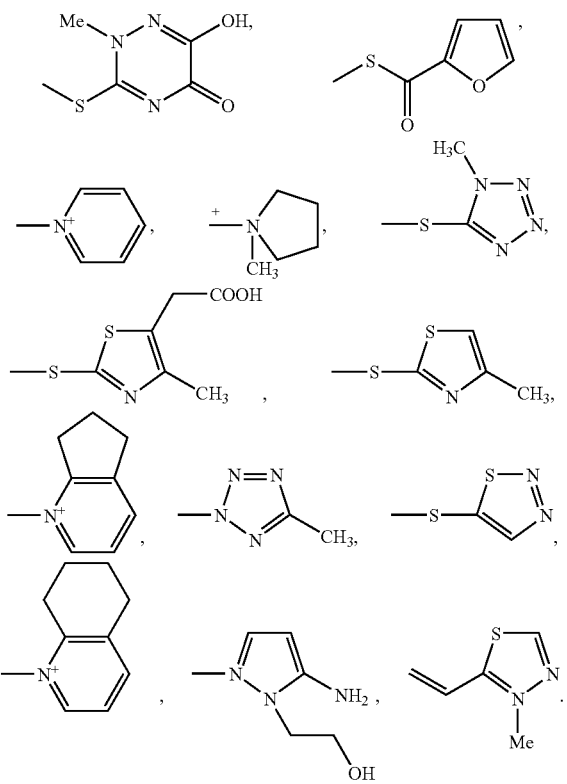

which comprises:
(i) activating the compound of formula (III) as acid chloride of formula (IIIa) in an organic solvent

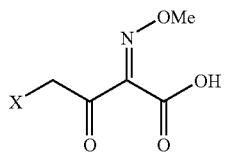

where X represents halogen atom such as chlorine or bromine, using an halogenating agent, (ii) treating the reaction mass obtained from step (i) with water at a temperature in the range of −40° C. to +10° C., (iii) separating the organic layer containing the activated derivative of formula (IIIa) and condensing the activated derivative of the formula (IIIa)

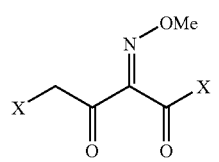

where X represents halogen atom such as chlorine or bromine, with 7-amino cephalosporin derivative of the formula (II) or silyl reactive derivative

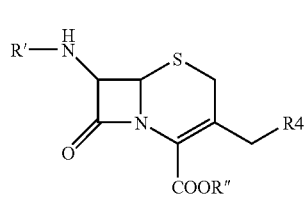

wherein R' represents hydrogen, or silyl and R" represents hydrogen or silyl in the presence of a solvent and in the presence or absence of base at a temperature in the range of −50° C. to 10° C. to produce a compound of formula (IV)

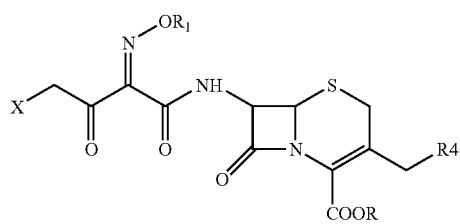

where all symbols are as defined above.

iv) optionally removing the solvent of step (iii) reaction mass and cyclizing the compound of formula (IV) with thiourea in the presence of water, in the presence or absence of water miscible solvent and base at a temperature in the range of −50 to 30° C. to produce compound of formula (I), wherein the improvement consists of producing the compound of formula (I), without isolating compound of formula (IV) and also characterised by one or more of the following improvements:

c) removing the solvent in step (iii),
d) conducting the reaction of step (iv) in homogeneous solvent system The starting material of the present invention can be prepared by utilizing the process available in the prior art.

The present invention is provided by the examples below, which are provided by way of illustration only and should not be considered to limit the scope of the invention.

EXAMPLE 1

Preparation of Ceftiofur

To the solution of 4-chloro-2-methoxyimino-3-oxobutyric acid (60.67 g) in dichloromethane (400 ml), phosphorus pentachloride (73.49 g) was added at −15 to −10° C. under nitrogen atmosphere. The reaction mass was stirred at −10 to −5° C. and washed with chilled purified water at 0-5° C. The organic layer was separated and added to a suspension of Furaca (100 g) in aqueous THF (20% & 1000 ml) by maintaining the pH at 5.5 to 8.5 using aqueous ammonia. To the reaction mixture was added thiourea (48 g) and the pH maintained in the range 5.0 to 8.0 using sodium bicarbonate. After completion of the reaction, reaction mass was acidified with TFA (40 ml) & the organic layer separated. To the organic layer sodium 2-ethylhexanoate (85 g) in THF was added and cooled to 0° C. The solid obtained was filtered and washed with THF and dried under vacuum to yield pure title compound. (80 g; purity by HPLC 98.4 to 98.98).

EXAMPLE 2

Preparation of Ceftiofur

To the solution of 4-chloro-2-methoxyimino-3-oxobutyric acid (60.67 g) in dichloromethane (400 ml), phosphorus pentachloride (73.49 g) was added at −15 to −10° C. under nitrogen atmosphere. The reaction mass was stirred at −10 to −5° C. and washed with chilled purified water at 0-5° C. The organic layer was separated and added to a silylated solution of Furaca (prepared by treating a suspension of Furaca (100 g) in dichloromethane (1000 ml) with N,O-Bis(trimethyl silyl)acetamide (135.8 g) at 20-30° C.) at −40 to −50° C. After completion of reaction dichloromethane was distilled out under vacuum at 20-30° C. To the residue THF (500 ml), DM water (500 ml) and thiourea (48 g) were added and pH maintained in the range of 5.0-8.0 using sodium bicarbonate solution at 2-5° C. After completion of the reaction, reaction mass was acidified with TFA (40 ml) & the organic layer separated. To the organic layer sodium 2-ethylhexanoate (85 g) in THF was added and cooled to 0° C. The solid obtained was filtered and washed with THF and dried under vacuum to yield pure title compound (100 g; purity by HPLC 99.12 to 99.54%).

EXAMPLE 3

Preparation of Ceftiofur

To the solution of 4-chloro-2-methoxyimino-3-oxobutyric acid (60.67 g) in dichloromethane (400 ml), phosphorus pentachloride (73.49 g) was added at −15 to −10° C. under nitrogen atmosphere. The reaction mass was stirred at −10 to −5° C. and washed with chilled purified water at 0-5° C. The organic layer was separated and added to a silylated solution of Furaca (prepared by treating a suspension of Furaca (100 g) in dichloromethane (500 ml) with TMCS (24.52 g) and HMDS (36.4 g) at 20-30° C. and stirring at 25-30° C.) at −40 to −50° C. After completion of reaction dichloromethane was distilled out under vacuum at 10-30° C. To the residue THF (500 ml), DM water (500 ml) and Thiourea (48 g) were added and stirred by maintaining pH at 5.0-8.0 using sodium bicarbonate at 2-5° C. After completion of the reaction reaction mass was acidified with TFA (40 ml) followed by layers were separated. To the organic layer sodium 2-ethyl-hexanoate (85 g) in THF was added and cooled to 0° C. The solid obtained was filtered and washed with THF and dried under vacuum to yield pure title compound (100 g; purity by HPLC 99.5%).

EXAMPLE 4

Preparation of Ceftiofur

To the solution of 4-chloro-2-methoxyimino-3-oxobutyric acid (60.67 g) in methylene dichloride(400 ml), phosphorus pentachloride (73.49 g) was added at −15 to −10° C. under nitrogen atmosphere. The reaction mass was stirred at −10 to −5° C. and washed with chilled purified water at 0-5° C. The organic layer was separated and added to a silylated solution of Furaca (prepared by treating suspension of Furaca (100 g) in dichloromethane (1000 ml) with N,O-Bis(trimethyl silyl) acetamide (135.8 g )at 10-20° C. and stirred to get clear solution) at −40 to −50° C. After completion of reaction dichloromethane was distilled out under vacuum at 25-30° C. To the residue THF (500 ml), DM water (500 ml) and Thiourea (48 g) were added and the pH maintained in the range of 5.0-8.0 using sodium bicarbonate at 18-22° C. After completion of the reaction, reaction mass was acidified with TFA (40 ml) and organic layer separated. To the organic layer sodium 2-ethylhexanoate (85 g) in THF was added and cooled to 0° C. The solid obtained was filtered and washed with THF, dried under vacuum to yield pure title compound (100 g, Purity by HPLC 99.1%).

EXAMPLE 5

Preparation of Ceftiofur

To the solution of 4-chloro-2-methoxyimino-3-oxobutyric acid (60.67 g) in dichloromethane (400 ml), phosphorus pentachloride (73.49 g) was added at −15 to −10° C. under nitrogen atmosphere. The reaction mass was stirred at −10 to −5° C. and washed with chilled purified water at 0-5° C. The organic layer was separated and added to a silylated solution of Furaca (prepared by treating suspension of Furaca (100 g) in dichloromethane (500 ml) with TMCS (24.52 g) and HMDS (36.4 g) at 10-20° C. and stirred to get clear solution at 25-30° C.) at −40 to −50° C. After completion of reaction dichloromethane was distilled out under vacuum at 25-30° C. To the residue THF (500 ml), DM water (500 ml) and thiourea (48 g) were added and stirred by maintaining pH at 5.0-8.0 using sodium bicarbonate at 18-22° C. After completion of the reaction, reaction mass was acidified with TFA (40 ml) and organic layer separated. To the organic layer sodium 2-ethylhexanoate (85 g) in THF was added and cooled to 0° C. The solid obtained was filtered and washed with THF, dried under vacuum to yield pure title compound (100 g, Purity by HPLC 99.5%).

EXAMPLE 6

Preparation of Ceftiofur

To the solution of 4-chloro-2-methoxyimino-3-oxobutyric acid (60.67 g) in methylene dichloride(400 ml), phosphorus pentachloride (73.49 g) was added at −15 to −10° C. under nitrogen atmosphere. The reaction mass was stirred at −10 to −5° C. and washed with chilled purified water at 0-5° C. The organic layer was separated and added to a silylated solution of Furaca (prepared by treating suspension of Furaca (100 g) in dichloromethane (500 ml) with TMCS (24.52 g) and HMDS (36.4 g) at 10-20° C. and stirred to get clear solution at 25-30° C.) at −40 to −50° C. After completion of reaction dichloromethane was distilled out under vacuum at 20-30° C. To the residue DM water (500 ml) and Thiourea (48 g) were added and stirred by maintaining pH at 5.0-8.0 using sodium bicarbonate at 18-22° C. After completion of the reaction, THF(1000 ml) was added and acidified with TFA (40 ml). The organic layer was separated. To the organic layer sodium 2-ethylhexanoate (85 g) in THF was added and cooled to 0° C. The solid obtained was filtered and washed with THF, dried under vacuum to yield pure title compound (100 g, Purity by HPLC 99.5%).

EXAMPLE 7

Preparation of Ceftiofur TFA Salt

To the solution of 4-chloro-2-methoxyimino-3-oxobutyric acid (60.67 g) in dichloromethane (400 ml), phosphorus pentachloride (73.49 g) was added at −15 to −10° C. under nitrogen atmosphere. The reaction mass was stirred at −10 to −5° C. and washed with chilled purified water at 0-5° C. The organic layer was added to a silylated solution of Furaca (prepared by treating a suspension of Furaca (100 g) in dichloromethane (500 ml) with TMCS (24.52 g) and HMDS (36.4 g) at 10-20° C. and stirred to get clear solution at 25-30° C.) at −40 to −50° C. After completion of reaction dichloromethane was distilled out under vacuum at 25-30° C. To the residue DM water (500 ml), THF (500 ml) and Thiourea (48 g) were added and stirred by maintaining pH at 5.0-8.0 using sodium bicarbonate at 18-22° C. After completion of the reaction, washed with Ethyl acetate and adjusted the pH to acidic using Trifluoro acetic acid (40 ml) at 0-5° C. The precipitated solid was filtered and washed with water dried under vacuum to yield pure title compound (160 g, Purity by HPLC 95.5% Content of TFA by IC 16.0-20.0%).

EXAMPLE 8

Preparation of Ceftiofur TFA Salt

To the solution of 4-chloro-2-methoxyimino-3-oxobutyric acid (60.67 g) in dichloromethane (400 ml), phosphorus pentachloride (73.49 g) was added at −15 to −10° C. under nitrogen atmosphere. The reaction mass was stirred at −10 to −5° C. and washed with chilled purified water at 0-5° C. The organic layer was added to a silylated solution of Furaca (prepared by treating a suspension of Furaca (100 g) in dichloromethane (500 ml) with TMCS (24.52 g) and HMDS (36.4 g) at 10-20° C. and stirred to get clear solution at 25-30° C.) at −40 to −50° C. After completion of reaction dichloromethane was distilled out under vacuum at 25-30° C. To the residue DM water (500 ml) and Thiourea (48 g) were added and stirred by maintaining pH at 5.0-8.0 using sodium bicarbonate at 18-22° C. After completion of the reaction, washed with Ethyl acetate and adjusted the pH to acidic using Trifluoro acetic acid (40 ml) at 0-5° C. The precipitated solid was filtered and washed with water dried under vacuum to yield pure title compound (160 g, Purity by HPLC 95.1% Content of TFA by Ion Chromatography 16.0-20.0%).

Preparation of Ceftiofur Sodium from Ceftiofur TFA Salt:

To the solution of Ceftiofur TFA salt in THF, triethylamine was added and adjusted the pH to 5.0-8.0. To the clear solution sodium 2-ethylhexonate in THF was added at 0-25° C. The solid obtained was filtered and dried to get Ceftiofur sodium (purity 99.3 to 99.7%) in pure form.

What is claimed is:

1. A process for the preparation of Ceftiofur of formula (I) or its salt

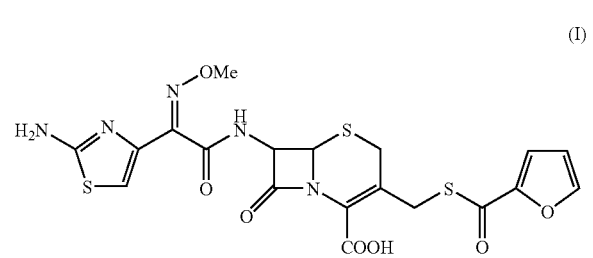

(I)

the process consisting of:

(i) activating the compound of formula (III) into a compound of formula (IIIa) in an organic solvent

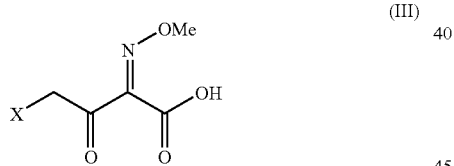

(III)

where X represents a halogen atom, using a halogenating agent, (ii) treating a reaction mass obtained from step (i) at a temperature in a range of −40° C. to 10° C. with water, (iii) separating an organic layer containing an activated derivative of formula (IIIa) and directly condensing the activated derivative of the formula (IIIa)

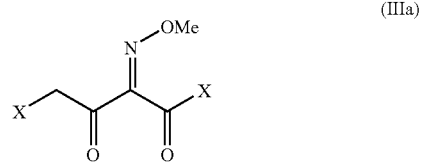

(IIIa)

where X represents a halogen atom, with 7-amino cephalosporin derivative of formula (II) or a trimethylsilyl reactive derivative of formula (II), wherein the organic layer from step (ii) containing the activated derivative of formula (IIIa) is condensed with a 7-amino cephalosporin derivative

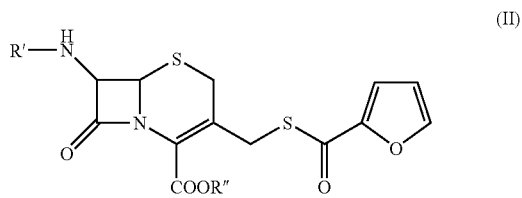

(II)

wherein R' represents hydrogen or trimethylsilyl, and R" represents hydrogen or trimethylsilyl, in the presence of a solvent and in the presence or absence of a base at a temperature in a range of −50° C. to 10° C. to produce a compound of formula (IV)

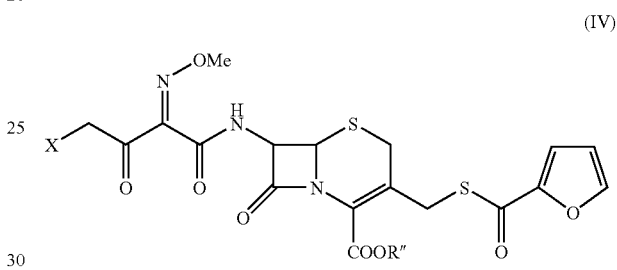

(IV)

where all symbols are as defined above, and iv) cyclizing the compound of formula (IV) with thiourea in the presence of water and in the presence or absence of a water miscible solvent and base at a temperature in a range of −50 to 30° C. to produce the compound of formula (I), wherein producing the compound of formula (I) occurs without isolating the compound of formula (IV) or its salt, and conducting the reaction of step (iv) in a homogeneous solvent system.

2. The process as claimed in claim 1, wherein the organic solvent in step (i) is selected from dichloromethane, ethyl acetate, N,N-dimethylformamide, N,N-dimethylacetamide and mixtures thereof and the solvent for condensation in step (iii) is selected from dichloromethane, ethyl acetate, methanol, ethanol, isopropanol, isobutyl alcohol, n-propanol, n-butanol, tert-butanol, tetrahydrofuran, aromatic hydrocarbons, acetone, ethyl methyl ketone, diethyl ketone, pentan-3-one, cyclohexanone, methyl isobutyl ketone, dioxane, acetonitrile, N,N-dimethylacetamide, dialkylethers, ethylene glycol, ethylene glycol monomethyl ether, diglyme, monoglyme, diethylene glycol, triethylene glycol, polyethylene glycol, water and mixtures thereof.

3. The process as claimed in claim 1, wherein the base in step (iii) is selected from the group consisting of ammonia, sodium carbonate, sodium bicarbonate, ammonium carbonate, barium carbonate, lithium carbonate, potassium carbonate, sodium hydroxide or potassium hydroxide, trimethyl amine, diisopropyl amine, and diisopropyl ethylamine.

4. The process as claimed in claim 1, wherein the water miscible solvent for the cyclization is tetrahydrofuran, acetone, ethyl methyl ketone, methyl isobutyl ketone, methyl isopropyl ketone, cyclohexanone, diethyl ketone, pentan-3-one, cyclohexane, acetonitrile, N,N-dimethylformamide, N,N-dimethylacetamide, dioxane, $(C_1-C_5)$alcohol, ethylene glycol, diglyme, monoglyme, ethylene glycol monomethyl ether, diethylene glycol, triethylene glycol, polyethylene glycol or mixtures thereof and the base in the cyclization is selected from sodium acetate, sodium carbonate, sodium bicarbonate, potassium acetate, ammonium acetate, ammonium carbonate, barium carbonate, calcium carbonate, potassium carbonate, barium carbonate, lithium carbonate, potassium bicarbonate, sodium methoxide, trimethyl amine, isopropyl amine, and sodium ethoxide.

5. Ceftiofur trifluoroacetic acid salt.

6. The process as claimed in claim 1, further comprising converting the compound of formula (I) into pharmaceutically acceptable salts, hydrates, solvates, esters or its prodrug.

7. The process as claimed in claim 1, wherein X represents chlorine or bromine.

* * * * *